(12) United States Patent
Siewert et al.

(10) Patent No.: US 12,076,253 B2
(45) Date of Patent: Sep. 3, 2024

(54) ORTHOSIS, ORTHOSIS OR PROSTHESIS COMPONENTS, AND METHOD FOR THE PRODUCTION THEREOF

(71) Applicant: Otto Bock Healthcare Products GmbH, Vienna (AT)

(72) Inventors: Gordon Siewert, Göttingen (DE); Etienne Overdevest, Göttingen (DE); Marco Volkmar, Duderstadt (DE)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 943 days.

(21) Appl. No.: 16/981,992

(22) PCT Filed: Mar. 15, 2019

(86) PCT No.: PCT/EP2019/056581
§ 371 (c)(1),
(2) Date: Sep. 17, 2020

(87) PCT Pub. No.: WO2019/179894
PCT Pub. Date: Sep. 26, 2019

(65) Prior Publication Data
US 2021/0030566 A1  Feb. 4, 2021

(30) Foreign Application Priority Data
Mar. 20, 2018  (DE) .................... 10 2018 106 573.6

(51) Int. Cl.
*A61F 5/00* (2006.01)
*A61F 2/50* (2006.01)
(Continued)

(52) U.S. Cl.
CPC .............. *A61F 2/5046* (2013.01); *A61F 2/80* (2013.01); *A61F 5/0102* (2013.01); *A61F 2002/5056* (2013.01)

(58) Field of Classification Search
CPC .. A61F 2/80; A61F 5/0102; A61F 2002/5056; A61F 2/78; A61F 2/50;
(Continued)

(56) References Cited

U.S. PATENT DOCUMENTS 4,417,569 A * 11/1983 Brudny ................. A61F 5/3753
602/20
5,288,287 A    2/1994  Castillo et al.
(Continued)

FOREIGN PATENT DOCUMENTS

DE   10 2012 002 552 A1   8/2013
JP      H09187471 A        7/1997
(Continued)

OTHER PUBLICATIONS

Okawara Akihiro, Pigeon-Breasted Corrective Orthosis, Feb. 1, 2018, All pages (Year: 2018).*
(Continued)

*Primary Examiner* — Kim M Lewis
(74) *Attorney, Agent, or Firm* — HOLLAND & HART LLP

(57) ABSTRACT

A method for producing orthosis or prosthesis components for receiving or for fastening to a body part, the method including: applying a base layer to a support corresponding in form to the form of the body part, arranging multiple fastening elements having a base and an interlocking element protruding from the base, on the base layer in defined positions relative to one another, the base of the fastening element resting on the base layer or facing towards the base layer, placing at least one layer of a fiber composite material on the base layer and embedding the base, the interlocking element remaining accessible from the side facing away from the base layer, and curing the at least one fiber composite material layer.

10 Claims, 19 Drawing Sheets

(51) Int. Cl.
*A61F 2/80* (2006.01)
*A61F 5/01* (2006.01)

(58) Field of Classification Search
CPC .... A61F 5/01; A61F 5/013; A61F 2005/0134; A61F 2/64; A61F 2002/30462; A61F 2220/0041; A61F 2220/0075; A61F 5/05858; A61F 5/0123; A61F 2005/0144
See application file for complete search history.

(56) References Cited

U.S. PATENT DOCUMENTS

| | | | |
|---|---|---|---|
| 5,334,442 A * | 8/1994 | Okamoto | B32B 5/26 442/224 |
| 5,891,071 A | 4/1999 | Stearns | |
| 6,342,043 B1 | 1/2002 | Gottsmann | |
| 7,708,709 B2 * | 5/2010 | Brewer | A61F 5/013 602/20 |
| 2008/0105994 A1 | 5/2008 | Stearns | |
| 2011/0015761 A1 | 1/2011 | Celebi et al. | |
| 2016/0310311 A1 * | 10/2016 | Haje | A61F 5/02 |

FOREIGN PATENT DOCUMENTS

| | | |
|---|---|---|
| JP | 2001523137 A | 11/2001 |
| JP | 2018015114 A * | 2/2018 |

OTHER PUBLICATIONS

Bartkus et al: "Composite prothesis joins performance, economy, comfort," Modern Plastics International 23, No. 7, Jul. 1993, pp. 39-41, 3 pages.

International Search Report for International Application No. PCT/EP2019/056581, mailed Jul. 15, 2019, 12 pages.

* cited by examiner

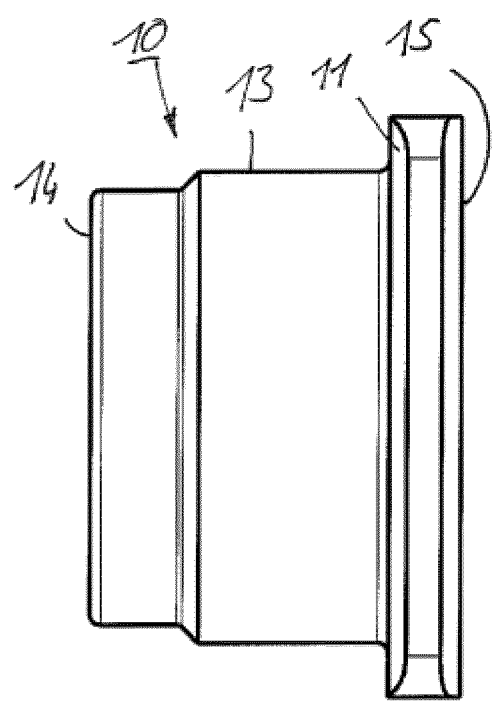

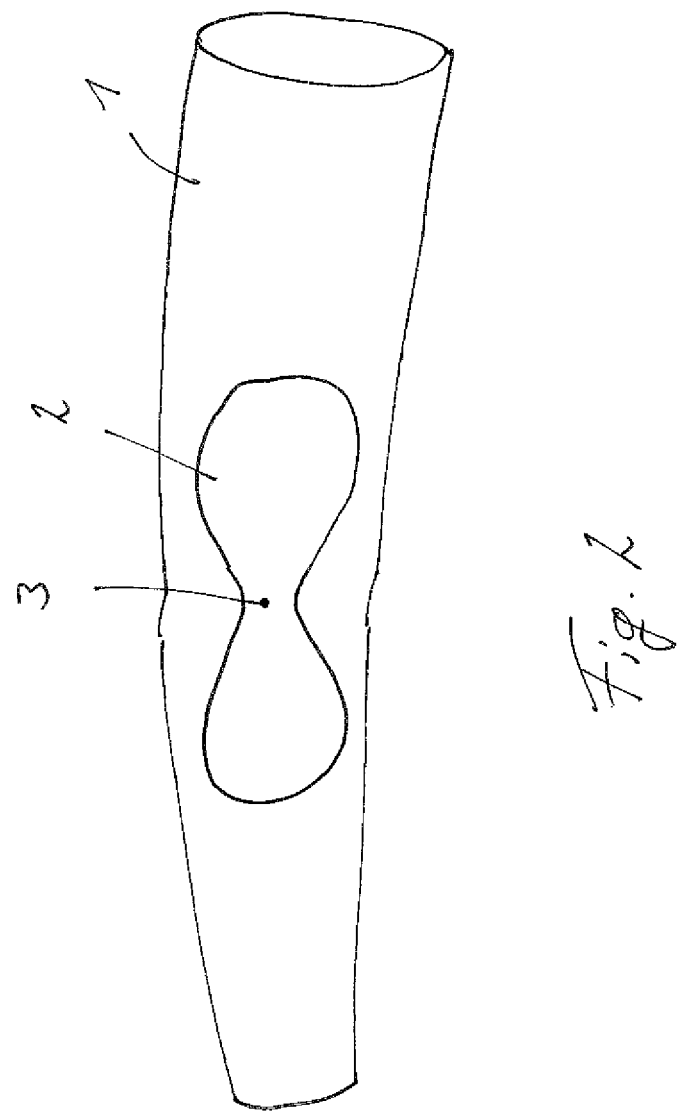

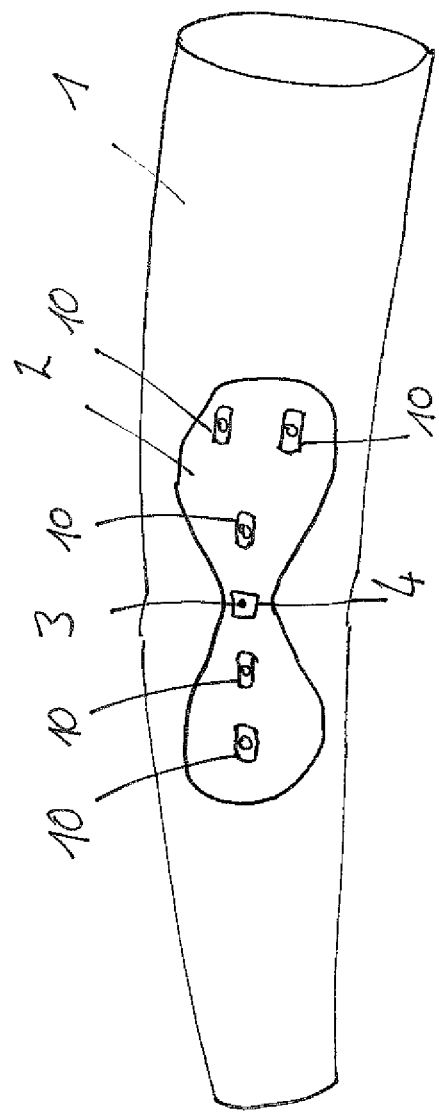

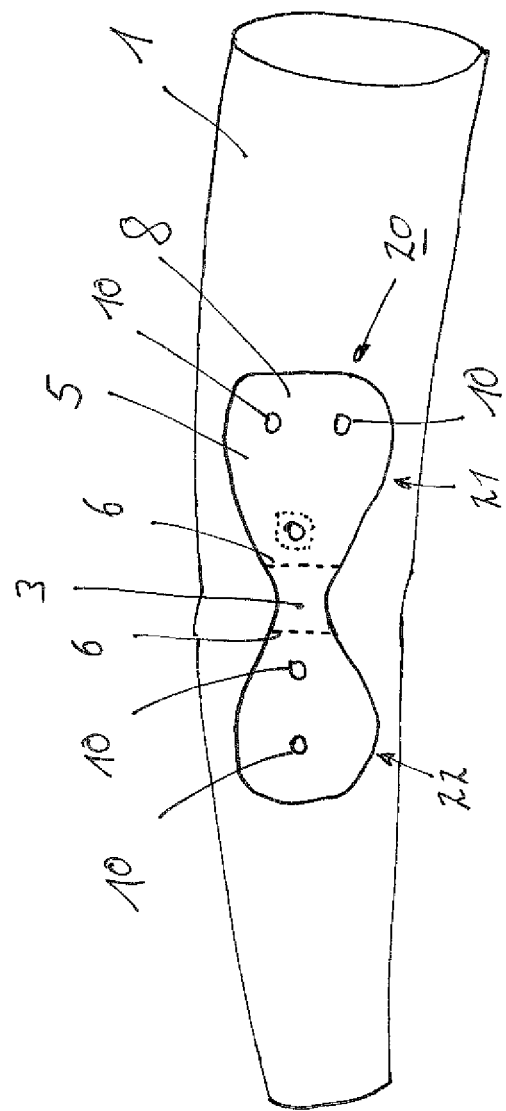
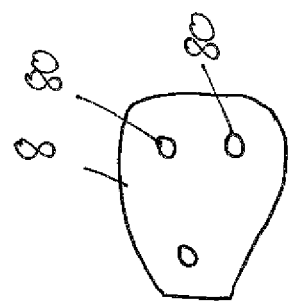
Fig. 4

ORTHOSIS, ORTHOSIS OR PROSTHESIS COMPONENTS, AND METHOD FOR THE PRODUCTION THEREOF

CROSS REFERENCE TO RELATED APPLICATIONS

This application is a U.S. National Entry and claims priority to PCT International Patent Application No. PCT/EP2019/056581, filed 15 Mar. 2019, and entitled "ORTHOSIS, ORTHOSIS OR PROSTHESIS COMPONENTS, AND METHOD FOR THE PRODUCTION THEREOF", which claims priority to Germany Patent Application No. 10 2018 106 573.6 filed 20 Mar. 2018, the entire disclosures of which are incorporated herein by this reference.

TECHNICAL FIELD

The invention relates to a method for the production of orthosis or prosthesis components for receiving or for fastening to a body part, and also to orthosis and prosthesis components, and to an orthosis composed of a plurality of orthosis components.

BACKGROUND

Orthosis or prosthesis components for receiving or for fastening to a body part are in particular prosthesis sockets, into which a stump of a limb is inserted, or orthosis shells or brackets, which are placed onto the body and fastened thereto in order to be connected, across a joint, to a second orthosis component via a joint device.

Prosthesis sockets are often produced from fiber-reinforced plastics which are placed onto supports, impregnated with resin and then cured. The supports can be designed as standard models or can be created on the basis of a cast of the respective stump. An anchor plate for securing a pyramid adapter or an adapter receptacle is cast in or fastened at a distal end of the prosthesis socket, such that the prosthesis socket can be connected to a distal joint device and to distal prosthesis components.

Orthosis components for receiving body parts or for fastening to body parts can be produced from plastic components. These components, which can be designed as shells or brackets or the like, can likewise be produced from fiber-reinforced plastic materials. The orthosis components can often be secured to the body part via fastening devices such as straps or buckles. By way of the fastening devices, the limb is enclosed and, if appropriate, the orthosis components are elastically deformed. Accordingly, the orthosis components are elastically deformable to a limited extent.

In order to produce orthoses with orthosis components for bearing on and receiving body parts or limbs, joint devices together with the orthosis components are secured and laminated on a model of the limb, in the case of individually tailored orthoses. Alternatively, fastening elements for joint devices are held in an orientation relative to each other via fixing devices, so-called dummies or space holders, which have to remain in situ during the curing and production of the orthosis components.

SUMMARY

The object of the present invention is to make available a method for the production of orthosis or prosthesis components for receiving a body part or for fastening to a body part, said method being able to be carried out more easily and more cost-effectively. The aim is to permit simple and safe fastening of joint components and functional components and to ensure that they are fastened according to requirements.

According to the invention, this object is achieved by a method and by the orthosis or prosthesis component or the orthosis composed of a plurality of such orthosis components disclosed herein. Advantageous embodiments and developments of the invention are disclosed in the description and the figures.

The method according to the invention for the production of orthosis components or prosthesis components for receiving a body part or for fastening to a body part involves firstly applying a base layer to a support that corresponds to the shape of the body part. The support can be configured as a cast of the body part, a modified cast of the body part, a molding of the body part or of a modified body part produced in some other way, or the body part itself. In the case of a cast, the modification can be made by removing or adding material or by applying a padding layer or, in the case of a support produced in another way, by modification of the data record such that, for example after optical detection or some other form of detection of the outer shape of the body part or of the stump, the data record is changed, for example smoothed, such that in the production of the physical support, for example by milling from a blank or by primary forming, for example by 3D printing, the corresponding support is produced. The base layer can be initially flexurally slack and of a curing type. Alternatively, provision is made that the base layer has such great inherent stability that, after forming on the support or onto the support, for example the cast, or after application to the body part as such, it does not change or does not appreciably change shape, particularly if the base layer is handled suitably carefully in the further course of handling. Before fastening elements are applied to the base layer, the base layer must have a sufficient inherent stability, which can be achieved by curing, if appropriate at elevated temperatures.

A plurality of fastening elements are then arranged on the base layer at defined positions relative to each other, wherein the fastening elements have a base from which at least one form-fit element protrudes. By way of the form-fit element, it is possible to secure further components of a prosthesis or orthosis to the prosthesis component or orthosis component, for example an actuator or a joint device. A form-fit element is also understood as a screw or a threaded rod. By arranging the fastening elements in previously defined positions relative to each other, it is possible to choose from a pool of components with standardized connection devices, in order then to secure them to the respective orthosis component or prosthesis component. It is thus possible, for example, to adapt orthosis components individually to the respective patient or orthosis user and to arrange different actuators or joint devices or also correction devices on the components in order, for example, to adapt to progress in the recovery process or to react to changes in circumstances, for example to worsening disorders. The base of the respective fastening element, in particular of all the fastening elements arranged on the base layer, either bears on the base layer or faces toward the base layer. The base preferably makes available an enlarged surface in relation to the form-fit element, in order to ensure better allocation and, if appropriate, introduction of force. The surface of the base facing toward the base layer can bear directly on the base layer or can be assigned to the base layer via an intermediate part, for example a spacer element or a formable, preferably curable compound. After the fastening elements have been arranged, at least one layer of a fiber composite material, for example of a prepreg, is applied to the base layer and the base embedded, wherein the form-fit element remains accessible from the side facing away from the base layer. By virtue of the accessibility of the form-fit element from the side facing away from the base layer, it is possible to secure a further component to the fastening element after the production of the orthosis component or prosthesis component. The at least one layer of the fiber composite material is then cured and the orthosis component or prosthesis component thus finished.

In a development of the method, provision is made that the base layer is connected to the at least one fiber composite material layer, and the base of the fastening element is laminated in between the base layer and the at least one fiber composite material layer. By means of the base layer being connected to or applied to the fiber composite material layer, the dimensionally stable orthosis component or prosthesis component is at least partially covered by a layer arranged on the inner face of the base of the fastening element. This prevents the fastening element from being able to be separated from the fiber composite material layer. The base layer itself can also be configured as a fiber composite material layer, for example from a prepreg, such that a permanent and rigid connection is provided for securing the fastening element with form-fit engagement to the inner face of the applied fiber composite material layer. The base layer can be removed from the at least one fiber composite material layer after production of the orthosis or the orthosis component.

In a development of the method, the form-fit element is formed or arranged on or in a shaft, wherein the shaft is partially embedded in the at least one fiber composite material layer and partially protrudes from the fiber composite material layer. The shaft protrudes from the base of the fastening element, wherein the base has a larger cross section than the shaft, such that a shoulder forms on which the applied layer of the fiber composite material bears. By virtue of the partial protrusion of the shaft, it is possible to keep the form-fit element easily accessible, so as to be able to secure the orthosis devices or prosthesis devices that are to be arranged on the orthosis component or prosthesis component.

The shafts of the plurality of fastening elements can be oriented parallel to each other. In particular, shafts of one group of fastening elements that are arranged on a particular orthosis device can be oriented parallel to each other. A particular orthosis component is, for example, an orthosis component which is arranged proximally or distally with respect to a joint axis, for example a thigh shell or thigh bracket and a lower-leg shell or lower-leg bracket. If the shafts of all of the fastening elements are oriented parallel to each other, this facilitates the mounting of the elements that are fastened or are to be fastened thereto, for example a joint device or actuator. The mutually parallel shafts of one group can be arranged tilted in relation to the parallel orientation of the shafts of another group.

In a further development of the invention, provision is made that at least one binding surface is arranged or formed on the fastening element, which binding surface is spaced apart from the base and is not covered by the at least one fiber composite material layer. The binding surface makes available a defined surface area for the arrangement of a further device, for example a damper or a joint device, and permits the precise allocation thereof and a firm connection thereof via the form-fit element. If all the binding surfaces of all the fastening elements on an orthosis component or prosthesis component are freely accessible, it is made easier to secure further components to the orthosis component if the corresponding contact surfaces or binding surfaces thereof likewise lie in one plane or are at least oriented parallel to each other. All of the binding surfaces preferably lie in one plane or are at least oriented parallel to each other in parallel planes, as a result of which a precise orientation of the device to be secured on the orthosis component or prosthesis component is possible.

The base of the fastening element can be fixed on the base layer, for example adhesively bonded, or fixed on the base layer using a filler compound. An adhesive layer, which is generally relatively thin, permits no or virtually no height compensation. Besides permanent fixing of the base of the fastening element and therefore of the fastening element itself to the base layer, a filler compound generally provides a height compensation in order to permit an allocation of all the fastening elements in a defined plane relative to each other or at least in a plane region relative to each other. All of the fastening elements are preferably oriented parallel to each other with respect to a reference plane, at least as regards the fastening elements on an orthosis component on a single limb part. A limb part is seen as a part of a limb that is connected, via a joint, to another limb part or to another body part.

In a development of the invention, provision is made that the support is configured as a positive model of the body part, and the curing of the at least one fiber composite material layer, if appropriate in conjunction with the connection of the base layer to the at least one fiber composite material layer, takes place on the support. On account of the arrangement and optionally the fastening and fixing of the fastening elements on the base layer, it is possible to preform the orthosis component or prosthesis component and to keep them oriented relative to each other without an additional fixing device or an external fixing element and to obtain the curing and stabilizing of the prosthesis component or orthosis component. If the base layer is sufficiently stable, the curing of the at least one fiber composite material layer can also take place without the support. For the final production of the orthosis component, further elements or components can be arranged on the orthosis component or prosthesis component, for example padding devices or the like.

In a development of the invention, provision is made that recesses are formed in the at least one applied fiber composite material layer, through which recesses parts of the fastening elements are guided, for example the shaft which protrudes from the base, or also form-fit elements which protrude from the base, such as projections, hooks or the like, via which a form-fit locking to the at least one fiber composite material layer and therefore an additional securing of the fastening element on the at least one composite material layer is achieved. By means of these additional formations or arrangements of projections on the base of the fastening element, the fastening element can be secured against rotation on or in the fiber composite material layer or orthosis component or prosthesis component.

In a development of the invention, provision is made that the fastening elements or the at least one fastening element are secured against rotation and fastened non-releasably to the orthosis component or prosthesis component. This can be achieved by the shaping of the base and/or of the shaft, which can be non-round, angular or equipped with projections or protruding elements. The non-releasability is achieved in particular by embedding the base and the form-fit element or the shaft in the at least one fiber composite material layer. In the base and/or in the form-fit element and/or the shaft, projections or recesses can be formed which come into form-fit engagement with parts of the fiber composite material layer, such that a rotation and/or displacement and axial shift in the longitudinal extent of the shaft is prevented.

The fastening elements can be covered completely by the base layer on the side of the orthosis component or prosthesis component facing toward the body part, such that a closed surface is present on the inner face, i.e. on the side facing toward the user of the prosthesis component or orthosis component, and this increases the wearing comfort. In addition, this prevents the fastening element from being pressed out of the orthosis component or prosthesis component in the direction of the orthosis user or prosthesis user.

In a development of the invention, provision is made that binding surfaces of all the fastening elements are pre-positioned in a common plane or in a region between two parallel planes, wherein the binding surfaces on the fastening elements are positioned spaced apart from the base. The orientation along parallel planes does not have to be provided for groups to the other side of the joint axis. A spacing optionally present between the bases of the fastening elements and the base layer is filled via a compensating element or via a compensating compound, so as to be able to work with predefined fastening elements. A fastening plane for the binding surfaces is thus predefined, or at least a region between two planes is predefined within which the binding surfaces of the fastening elements have to be located. The distance present between the bases of the standardized, predefined fastening elements and the base layer which is configured individually to the respective user of the orthosis component or prosthesis component is then compensated via a compensating element or a compensating compound. The compensating element can serve at the same time for fixing on the base layer; the same applies to the compensating compound, which is configured for example as a filler compound or as a curable adhesive having a sufficient strength and stability to hold the fastening elements on or in the orthosis component or prosthesis component.

In a development of the method, provision is made that the fastening elements are pre-positioned in predetermined positions relative to each other and to a joint axis of a joint of the body part and are arranged on or at least assigned to the base layer. If direct contact between the respective base and the base layer is possible, the positioning and optionally the fixing is carried out without interposition of a compensating element or a compensating compound; if this is not possible, the spacing between the base and the base layer is compensated via a compensating element or a compensating compound. The fixing is obtained either via the filler compound or via an adhesive which forms no connecting layer or no appreciable connecting layer between the base and the base layer. The positions of the fastening elements relative to each other and in particular the positions of binding surfaces of all the fastening elements on a common orthosis component are predefined and correspond to the fastening devices or binding points of components which are arranged or are intended to be arranged on the orthosis component or prosthesis component.

The fastening elements can be arranged on a holder or a positioning device and pre-positioned relative to each other before they are arranged on or allocated to the base layer. After the fastening elements have been arranged on the base layer or allocated to the base layer and the fastening elements have been fixed on the base layer, the holder or the prosthesis device is removed.

In a development of the method, provision is made that in order to form an orthosis with a distal component and a proximal component, the at least one fiber composite material layer, which is applied to the base layer and embeds the base, is arranged in a region on the support corresponding to that of a natural joint and is then cured in order to form a main body. Before the curing, fastening elements are arranged proximally and distally from a joint axis of the natural joint and are embedded in the at least one fiber composite material layer. After the curing, the at least one fiber composite material layer of the main body and if appropriate also the base layer, if the latter is cured together with the applied fiber composite material layer, is separated in the region of the joint axis, in order to form from the main body the distal component and the proximal component of the orthosis. If no fiber composite material layer is applied to the base layer in the region of the joint axis, an orthosis main body with fastening elements secured thereon can likewise be obtained, wherein the region about the joint axis is formed only by the base layer. For separation and division into a proximal component and a distal component, only the base layer then has to be removed. Instead of the embodiment and design of two orthosis components on one support for producing an individual orthosis, an orthosis main body that spans a joint is produced, which is cured. In the orthosis main body, the fastening elements are secured for arranging a joint device or an actuator on the outside, wherein the securing of the fastening elements takes place at predetermined, standardized positions in predetermined orientations relative to each other. Both the orientation of the fastening elements or of the fastening element on the proximal component and the orientation of the fastening elements or of the fastening element on the distal orthosis component are predetermined and move within a predefined tolerance range.

Binding surfaces are preferably defined on the fastening elements, which binding surfaces are oriented parallel to each other and more preferably in a common plane in the respective orthosis component, i.e. in a proximal orthosis component and in a distal prosthesis component. The orientation of the binding surfaces on different components is likewise predefined and lies in a predefined tolerance range, in order to facilitate a facilitated allocation of the further components, in particular the joint device and an actuator.

All the binding surfaces of a component are preferably tilted about the same angle with respect to the orientation of the planes of the binding surfaces of the other component if tilting is needed, for example on account of the particular shape of the limb on which the joint-spanning orthosis is intended to be placed. After the arrangement in defined positions relative to each other and in a defined angle orientation within a certain tolerance range relative to each other, a separation process is then carried out in the region of the joint axis of the natural joint of the joint-spanning main body in order to separate the main body into a proximal component and into a distal component, in order thereafter to secure a joint device on the proximal component and the distal component via the fastening elements and to produce the orthosis. Of course, after the curing and the separation, further working of the orthosis components can take place, for example smoothing of the shape, deburring of the edges, and sealing, painting and padding, and also the fastening of fastening devices such as straps or the like.

To produce the orthosis with the orthosis components produced in the manner described above, a joint device is secured to the fastening elements via the form-fit elements, for example screwed on if the form-fit elements have a thread.

The orthosis or prosthesis component according to the invention for receiving a body part or for fastening to a body part has a base layer which can be arranged on a support shaped in a manner corresponding to the shape of the body part, wherein the support can be both the body part itself and also an impression or a model of the body part. At least one fastening element with a base and with a form-fit element protruding from the base is arranged on the base layer, wherein the base bears on and faces toward the base layer. The fastening element is embedded with at least one layer, preferably a plurality of layers of a fiber composite material, and the form-fit element remains accessible from the side facing away from the base layer after the fiber composite material layer or fiber composite material layers have been cured In a development of the invention, provision is made that a plurality of fastening elements are embedded which have a shaft as form-fit element or with a form-fit element and at least one non-embedded binding surface, wherein the shafts of all the fastening elements of an orthosis component or of a prosthesis component are oriented parallel to each other. By arranging the shafts parallel to each other, it is possible to simplify the mounting of further components on the fastening element. The fastening elements are preferably arranged in groups, for example a group for the proximal component and a group for the distal component. The orientation of the fastening elements within a group is preferably uniform.

Binding surfaces are likewise arranged parallel to each other, such that corresponding binding surfaces on components which are secured to the orthosis components or prosthesis components can be easily oriented relative to each other and can be secured thereon in an easily exchangeable manner. All of the binding surfaces can be arranged in parallel or even in a common plane. Similarly, the binding surfaces of individual groups can be arranged in parallel or in a common plane. All of the binding surfaces of an orthosis component or prosthesis component preferably lie in a common plane or at least between two mutually parallel planes that are offset relative to each other. The common planes can also be tilted relative to each other and can be oriented relative to each other at an angle deviating from 180°.

The base layer can likewise be configured as a fiber composite material layer and can form a closed surface on the side of the orthosis component or prosthesis component facing toward the body part.

The fastening element can be embedded non-releasably in the at least one fiber composite material layer and in a manner secure against rotation.

The fastening element can have a non-round base and/or projections and/or recesses for the securing against rotation, which are embedded with form-fit engagement in the at least one fiber composite material layer and are held thereon.

A thread can be arranged and formed on the form-fit element or on the shaft. The thread can be configured either as an inner thread or outer thread, such that the fastening element acts as an anchoring screw or anchoring nut.

Fastening devices for securing the orthosis component or prosthesis component to a body part can be arranged on the orthosis component or prosthesis component, for example straps, buckles or also prosthesis liners for the implementation of suction socket technology.

An orthosis composed of a plurality of orthosis components, as have been described above, has at least one joint device secured to a plurality of fastening elements. An actuator can likewise be secured to a proximal orthosis component and to a distal orthosis component via fastening elements.

In a development of the orthosis, provision is made that the orthosis components are connected to each other to span a natural joint and have a predetermined separation point or a predetermined separation region in which the joint axis of the natural joint lies.

BRIEF DESCRIPTION OF THE DRAWINGS

An illustrative embodiment of the invention is explained in more detail below with reference to the attached figures, in which:

FIGS. 1a to 1d show views of a fastening element;

FIG. 2 shows a schematic perspective view of a support with an applied base layer;

FIG. 3 shows a base layer according to FIG. 2 with applied fastening elements;

FIG. 4 shows a schematic side view with an applied fiber composite material layer;

DETAILED DESCRIPTION

Figure 1A:
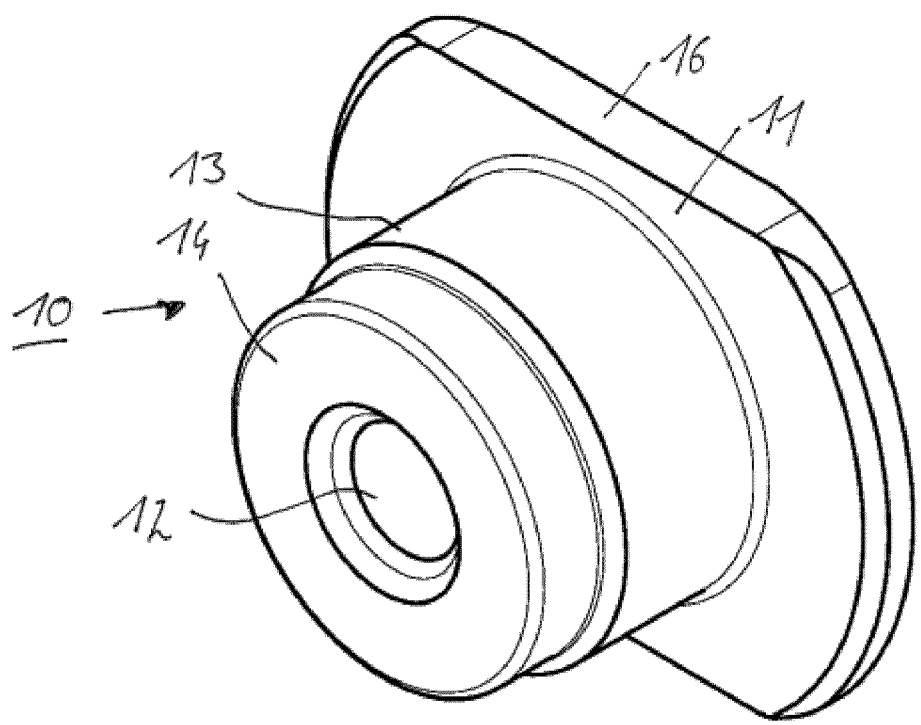
Figure 1B:
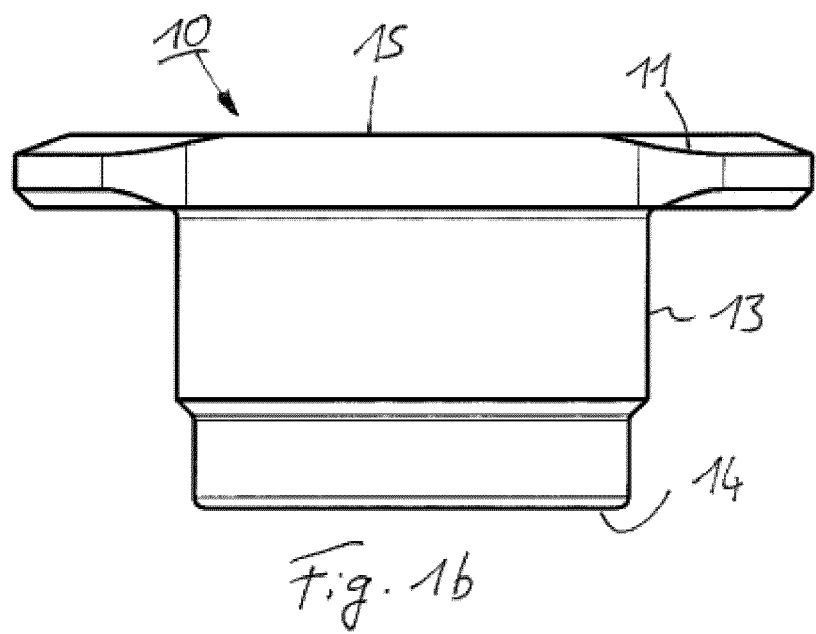
Figure 1C:
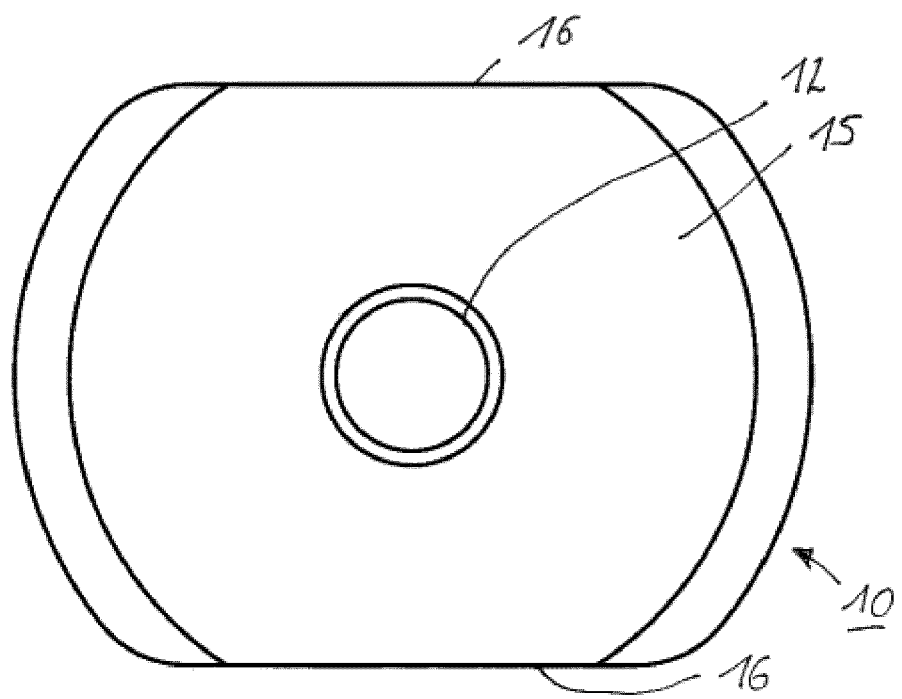

FIGS. 1a to 1d show different views of a fastening element 10, wherein FIG. 1a shows a perspective overall view, FIG. 1b shows a side view, FIG. 1c shows a bottom view, and FIG. 1d shows a further side view. The fastening element 10 has a base 11 which, in the illustrative embodiment shown, is substantially flat and plate-shaped. Bevels are formed at the edges of the base 11 in order to provide improved contact to a substrate or a support surface in order to form a smooth transition. In addition, connecting material or adhesive can be arranged between the bevels and fiber composite materials in order to fix the fastening element 10 thereon. The base 11 is non-round and has two flattened regions 16 at mutually opposite sides. Between the flattened regions 16, the base 11 forms a radius, the continuation of which would lead to a circle shape. The contour of the base 11 thus corresponds to a circle with cut-off circle segments with parallel chords. A central bore with a form-fit element 12 in the form of an inner thread is formed in the middle of the base 11. The inner thread 12 extends along the longitudinal extent of a shaft 13, which protrudes from the base 11. A binding surface 14, which is substantially plane, is formed on the side of the shaft 13 remote from the base 11. Lying opposite the binding surface 14, a bottom surface 15 is formed on the base 11; the binding surface 11 and the bottom surface 15 are oriented substantially parallel to each other. The shaft 13 is rotationally symmetrical, and the central bore with the inner thread 12 is formed coaxially with respect to the longitudinal extent of the shaft 13. The shaft 13 is provided with a shoulder in the front third directed toward the binding surface 10, that is to say the shaft 13 there has a smaller diameter than in the region of the base 11. The size of the shoulder can vary. In particular, the shoulder is chosen such that layers of a fiber composite material applied to the base 11 reach as far as this shoulder or at least do not reach beyond the shoulder in the direction of the binding surface. The outer contour of the shaft 13 can also have other outer contours, in particular a non-rotationally symmetrical outer contour in order to secure against rotation in addition to the securing against rotation provided by the non-round configuration of the base 11.

Recesses, projections or undercuts can also be arranged or formed on the fastening element 10, in order to provide further securing to a base layer for producing a main body for an orthopedic device. The use of the fastening element 10 in connection with the production of orthopedic devices such as orthoses, prostheses or other orthopedic components is explained below. The base 11 serves to secure the fastening element 10 on a main body, while the form-fit element 12 serves to ensure that further components of an orthopedic device can be secured to the fastening element 10, for example joints, actuators, dampers or other devices or components.

The production of an orthosis as an orthopedic device is explained in more detail with reference to FIGS. 2 to 4.

FIG. 2 shows a schematic view of a support 1 which is shaped corresponding to the body part on which an orthosis or prosthesis is intended to be worn. In the illustrative embodiment shown, the support 1 is formed as a part of a leg with a thigh portion, a knee joint and a lower leg portion. As an alternative to an embodiment in the form of a leg, the support can also be configured in the form of an arm or part of an arm. It is also possible to configure the support 1 in any other form that is required in order to form an orthosis. If a prosthesis is to be produced, the support 1 can correspond only partially to the shape of the body of the patient or prosthesis user, i.e. where the stump is still present. The distal part of the support is then modeled, for example using a 3D computer method or in some other way.

A base layer 2, which is formed from one or more blanks, is applied to the support 1. The base layer 2 is preferably formed from a fiber composite material, for example from a prepreg or from another fiber composite material. In the illustrative embodiment shown, the base layer 2 is formed in one piece and extends over a joint axis 3 of a natural or assumed joint of the respective limb. In the illustrative embodiment shown with the support 1 as a thigh part, the base layer 2 covers the knee-joint axis 3. The base layer 2 is sufficiently flexible to be able to conform to the surface contour of the support 1. The support 1 can be modified according to the actual contour of the limb, for example by addition of material, smoothing of a 3D model or the like, for example in order to be able to arrange padding elements on the inner face of the orthosis or prosthesis that is to be produced. In the case of a prosthesis, it may be necessary for the prosthesis socket or the receiving device to be chosen larger, so as to be able to receive liners or other protective coverings without exerting too great a pressure on the body part.

The base layer 2 is of a closed configuration, i.e. not open for the passage of components such as fastening elements 10 that are applied to the base layer 2. The base layer 2 can be fixed to the support 1 either mechanically or by an adhesive. The fixing is done in such a way that the base layer 2 is removable again after the orthosis or prosthesis has been produced.

FIG. 3 shows a next phase in the production of the orthosis components, in which phase fastening elements 10, as have already been described with reference to FIG. 1, are placed on the lateral surface of the base layer 2, i.e. on the surface facing away from the support 1. The fastening elements 10 are applied via the underside 15, i.e. the surface of the base 11 facing away from the abutment surface 14 The fastening elements 10, in the illustrative embodiment five fastening elements 10, of which two are positioned in the distal region and three in the proximal region, are positioned on the base layer 2 preferably via a positioning device. The positioning device is explained in more detail further below. By means of the positioning device, the fastening elements 10 are arranged on the base layer 2 at defined spacings from each other and from the joint axis 3. The positioning device is secured to or placed on a receptacle 4, for example plugged on, screwed on or fixed via a magnetic lock. The receptacle 4 is preferably already arranged on the support 1 and protrudes through a recess in the blank of the base layer 2. The receptacle 4 can be worked into the support 1, for example cast in or inserted. It preferably has a thread, a sleeve or a peg, of which the longitudinal extent coincides with the knee-joint axis. Generally speaking, the longitudinal extent of the receptacle 4 should coincide with the joint axis about which an orthosis upper part pivots relative to an orthosis lower part or a proximal component pivots relative to the distal component of the orthosis.

The fastening elements 10 are fixed on the base layer 2, for example by an adhesive, a filler compound, or by using a compensating material. The aim is that the fastening agent, such as filler or adhesive, does not deform during the subsequent processing of the orthosis. To produce the orthosis, the latter can be cured at high temperatures and under vacuum, which must not cause displacement of the fastening elements 10 or tilting of the fastening elements 10.

After all of the fastening elements 10 have been fastened on the base layer 2, the positioning device is removed, as will be explained in detail later. The fastening elements 10 and also the receiving device 4 remain securely on the outer or lateral surface of the base layer 2.

At least one layer 8 of a fiber composite material with punched-out recesses is then placed over the shafts of the fastening elements 10, wherein the recesses in the layer 8 of a fiber composite material are dimensioned such that the respective shaft can pass through, but not the base 11. In this way, the base 11 of the fastening elements 10 is embedded between the base layer and an outer composite fiber material layer 8. Predetermined separation lines 6, along which separation can take place easily or more easily, can be worked into the outer fiber composite material layer 8. In the illustrative embodiment shown, two predetermined separation lines 6 form a predetermined separation region in which the joint axis 3 and also the receiving device 4 lies before the anchor plate. After the separation at the predetermined separation lines 6, a proximal component 21 and a distal component 22 of the orthosis are obtained, i.e. a thigh shell 21 and a lower-leg shell 22, with fastening elements 10 laminated therein. The separation or removal of the predetermined separation region between the predetermined separation lines 6 is effected only after the base layer 2 together with the at least one fiber composite material layer 8 has been bonded to the outside and then secured on top of each other. This takes place, for example after application of an underpressure, in an oven at elevated temperatures. The fiber composite material layers 8 are preferably applied as far as the shoulder in the shaft 13. The shoulder ensures that a sufficient material thickness is present in the region of the fastening elements. A fiber composite material layer 8 as blank with pre-formed recesses 80, which correspond in terms of diameter to the shaft diameters of the shafts 13 and in terms of their positions to the positions of the fastening elements 10 on the base layer 2, are shown on the left in FIG. 4.

After the laminate material has cured and cooled, a main body 20 is present with a continuous base layer 2 on the inner side, fastening elements 10 placed thereon, and at least one layer, preferably a plurality of layers, of fiber composite material 8 which are connected to each other such that the fastening elements 10 are laminated in. After curing and cooling, the orthosis main body 20 is separated, for example sawn through, in the region of the predetermined separation points 6, in order to separate the thigh shell or proximal orthosis component 21 from the lower-leg shell or distal orthosis component 22. The orthosis components 21, 22 are then removed from the support 1, optionally re-worked and ground, provided with receptacles for fastening devices such as straps, and equipped with the necessary attachments such as joint devices, dampers or pads.

Figure 5:
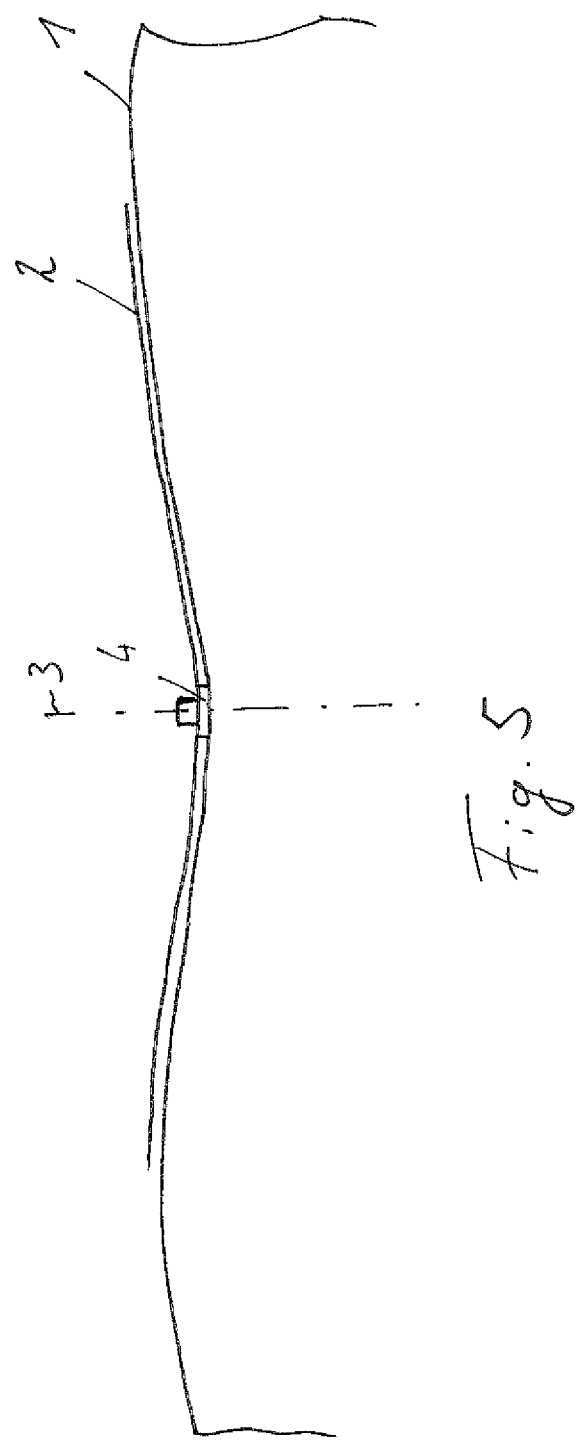
FIG. 5 shows a sectional view according to FIG. 2.
Figure 6:
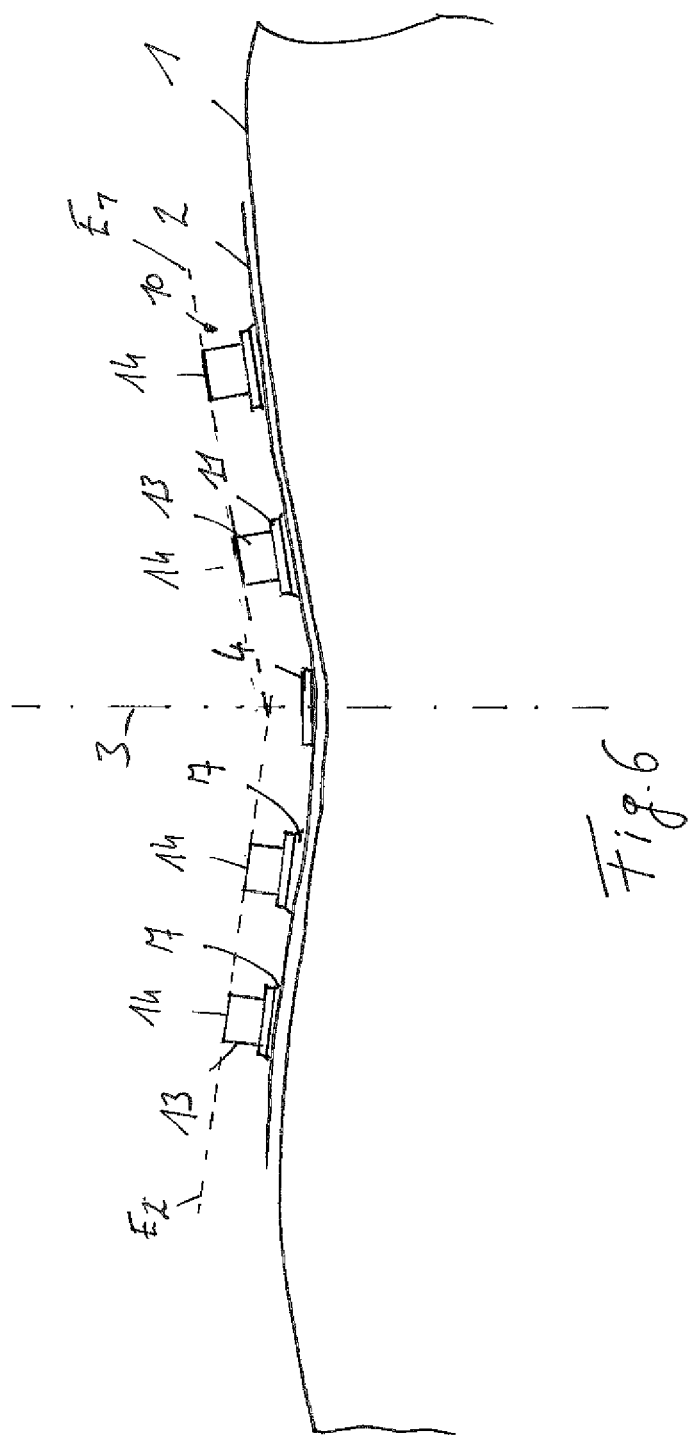
FIG. 6 shows a sectional view according to FIG. 3.
Figure 7:
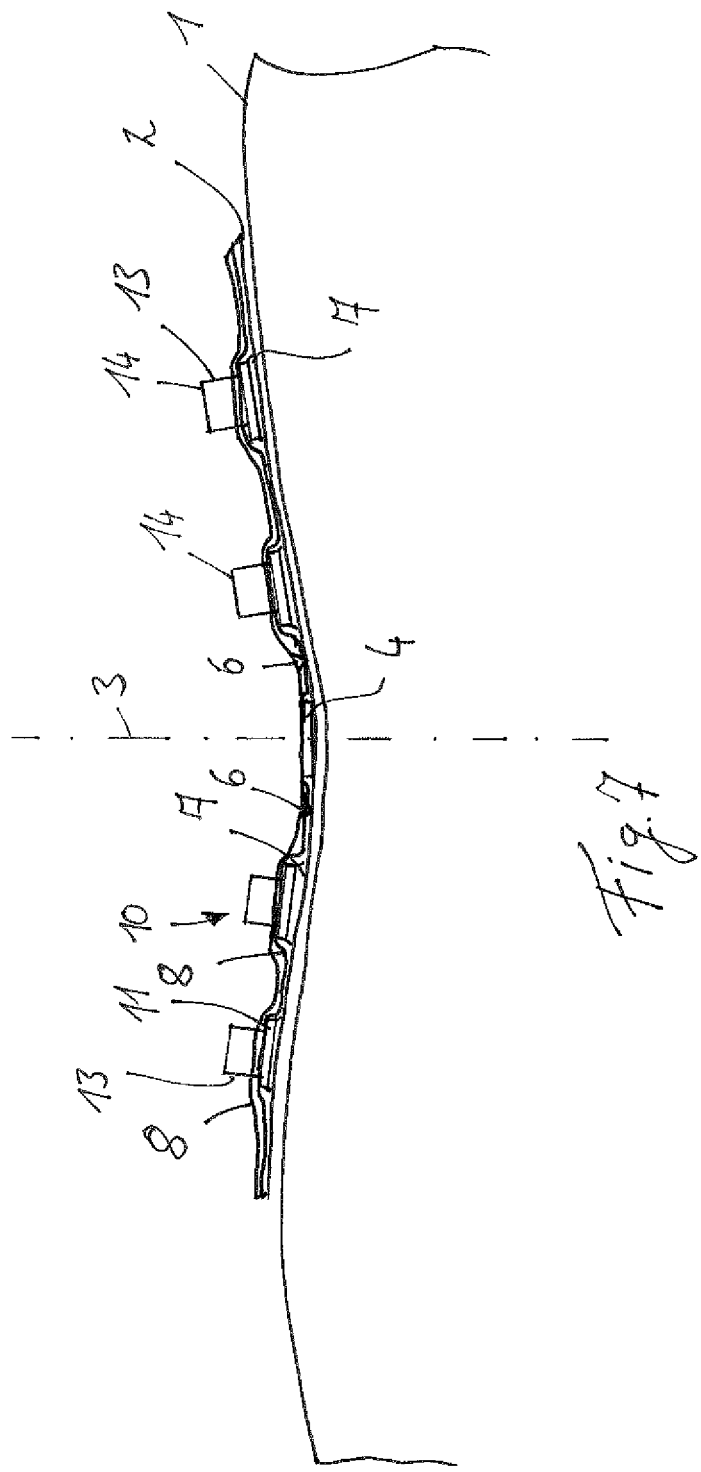
FIG. 7 shows a sectional view according to FIG. 4.

FIGS. 5 to 7 show the production sequence in a schematic sectional view. First, the anchor plate or the receptacle 4 is positioned on the support 1, specifically in the region of the joint axis of the natural joint or of a compromise axis 3. The base layer 2 is then applied to the outer or lateral surface of the support 1 and optionally fixed. The material of the base layer 2 can be plastically deformable and have low restoring forces, so as to allow it to bear as fully as possible on the outer surface of the support 1. The spacing from the support 1 is indicated in order to make matters clearer.

FIG. 6 shows the state after the fastening elements 10 are applied to the lateral surface of the base layer 2. The fastening elements 10 are positioned on the base 2, in a manner aligned with the joint axis 3, via a positioning device. It will be seen that the respective bases 11 of the fastening elements 10 should be arranged as close as possible to the surface of the base layer 2. In the illustrative embodiment shown, the connection of the respective underside 15 of the respective base 11 of the fastening elements 10 is effected via a filler compound 7, which at the same time evens out irregularities in the surface of the base layer 2 and ensures that the fastening elements 10 are rigidly anchored on the base layer 2.

It will be seen from FIG. 6 that all of the binding surfaces 14 lie in a respective plane E1, E2, wherein the plane E1 stands for the fastening elements 10 of the proximal component 21 and the plane E2 stands for the fastening elements of the distal component 22. It will be seen from FIG. 6 that the planes E1, E2 in the illustrative embodiment shown do not lie parallel to each other or form a common plane. This would be the case if for example, in the illustrative embodiment, there were a completely straight leg on the lateral side or medial side. A more natural depiction is shown in which there is a lateral curvature both of the thigh and of the lower leg starting from the knee joint. In the illustrative embodiment shown, both planes E1, E2 intersect each other in the joint axis 3, thus resulting in a common section line, which is preferably orthogonal to the joint axis 3. It is also possible that the binding surfaces do not lie exactly in a plane E1, E2, and instead there is a certain vertical offset. It is likewise possible that the planes E1, E2 do not intersect each other in the joint axis 3, for example because a vertical offset has been established. All the binding surfaces 14 of all the fastening elements 10 of an orthosis component 21, 22 preferably lie on a common plane E1, E2. The longitudinal extents of all the bores, pegs or form-fit elements 12 such as inner threads or outer threads in the fastening elements 10 are preferably oriented parallel to each other, in each case with respect to an orthosis component. That is to say, all the longitudinal axes of the fastening elements 10 on the proximal orthosis component 21 are preferably oriented parallel to each other, likewise the longitudinal extents or longitudinal axes of the fastening elements 10 on a distal orthosis component 22.

After the fastening elements 10 have been secured on the base layer 2, several layers 8 of a composite fiber material are applied, as shown in FIG. 7, for example resin-impregnated fiber mats, optionally with addition of further adhesives, hardeners, solvents or the like. The layers 8 of the fiber composite material or of the fiber composite materials can be applied in different orientations, in order to laminate in the bases 11 of the fastening elements 10. For this purpose, recesses 80 or punched holes corresponding to the shape and the diameter of the respective shafts 13 are formed in the blanks of the fiber composite material layer 8. Since the bases 11 are greater than the diameters of the shafts 13, no fastening element 10 can be removed from the respective orthosis component 21, 22 after the fiber composite material layers 8 have been connected to the base layer 2. On account of the non-round configuration of the base 11, all of the fastening elements 10 are secured against rotation. To increase the securing against rotation, it is possible for projections, hooks, undercuts or the like to be provided, so that the fastening elements 10 cannot rotate after the orthosis components 21, 22 have been produced.

The binding surfaces 14 are not all covered by a fiber composite material layer 8, so as to ensure accessibility to the form-fit elements 12 and to ensure a defined bearing of the components that are to be mounted. In order to avoid contamination of the form-fit element 12, it can be secured. In the embodiment according to FIG. 1, in which the form-fit element 12 is designed as an inner thread, this can be achieved for example by a screw which is unscrewed after the orthosis component has been produced. If the form-fit element 12 is designed as an outer screw, a screw cap can be screwed on in order to protect the thread. The same applies to other form-fit elements such as pegs, bores or the like. After the fiber composite material layers 8 have been applied, the orthosis main body 20 is produced on the support 1 under vacuum and at elevated temperatures. The predetermined separation points 6 are formed proximally and distally at the joint axis 3, for example by impressions or cuts made in the fiber composite material layers 8 or simply by applying no or fewer fiber composite material layers 8 in the region between the predetermined separation points 6.

After curing and separation of the orthosis components 21, 22 from each other, other components can be secured to the fastening elements 10.

Figure 8:
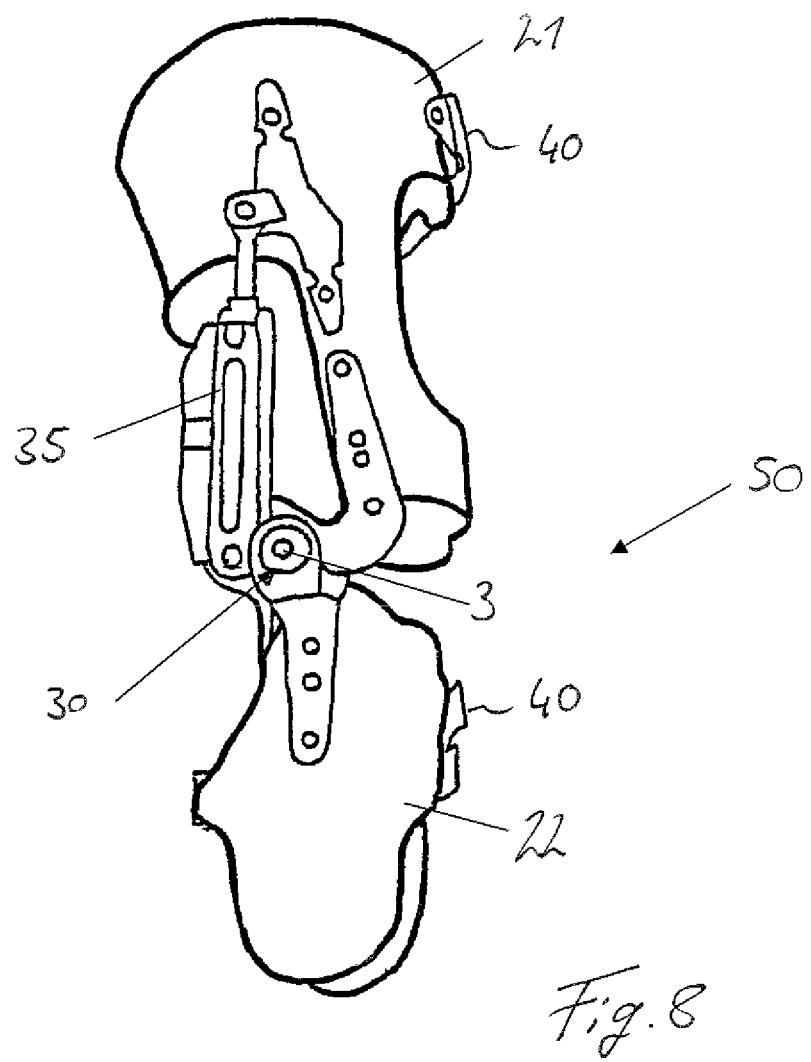
FIG. 8 shows a view of a finished orthosis.

FIG. 8 shows a variant of a knee-joint orthosis in which the proximal component 21 is designed as a thigh shell and the distal component 22 as a lower-leg shell. Fastening devices 40, which are designed as straps, are arranged on both orthosis components 21, 22 in order to secure the orthosis 50 to a leg. A joint device 30 with a hydraulic actuator 35 is secured to the no longer visible fastening elements, for example via screws. The joint device 30 has its pivot axis in the region of the joint axis of the natural joint. The position of the joint axis 3 on the joint device 30 is made safe by the exact positioning of the fastening elements relative to the joint axis 3 of the natural joint via a positioning device. The design of the orthosis components 21, 22 in the form of the orthosis shells is adapted very effectively and individually to the shape of the respective orthosis wearer. The production of the orthosis can take place without previously arranging the joint device 30 or a hydraulic component 35 on the orthosis components 21, 22, which is extremely advantageous in respect of the high temperatures and negative pressures arising during manufacture, in particular for electronic controls. The nature of the manufacturing prevents any limit on the attachment parts that are to be used, such as dampers, controls or the like.

Figure 9:
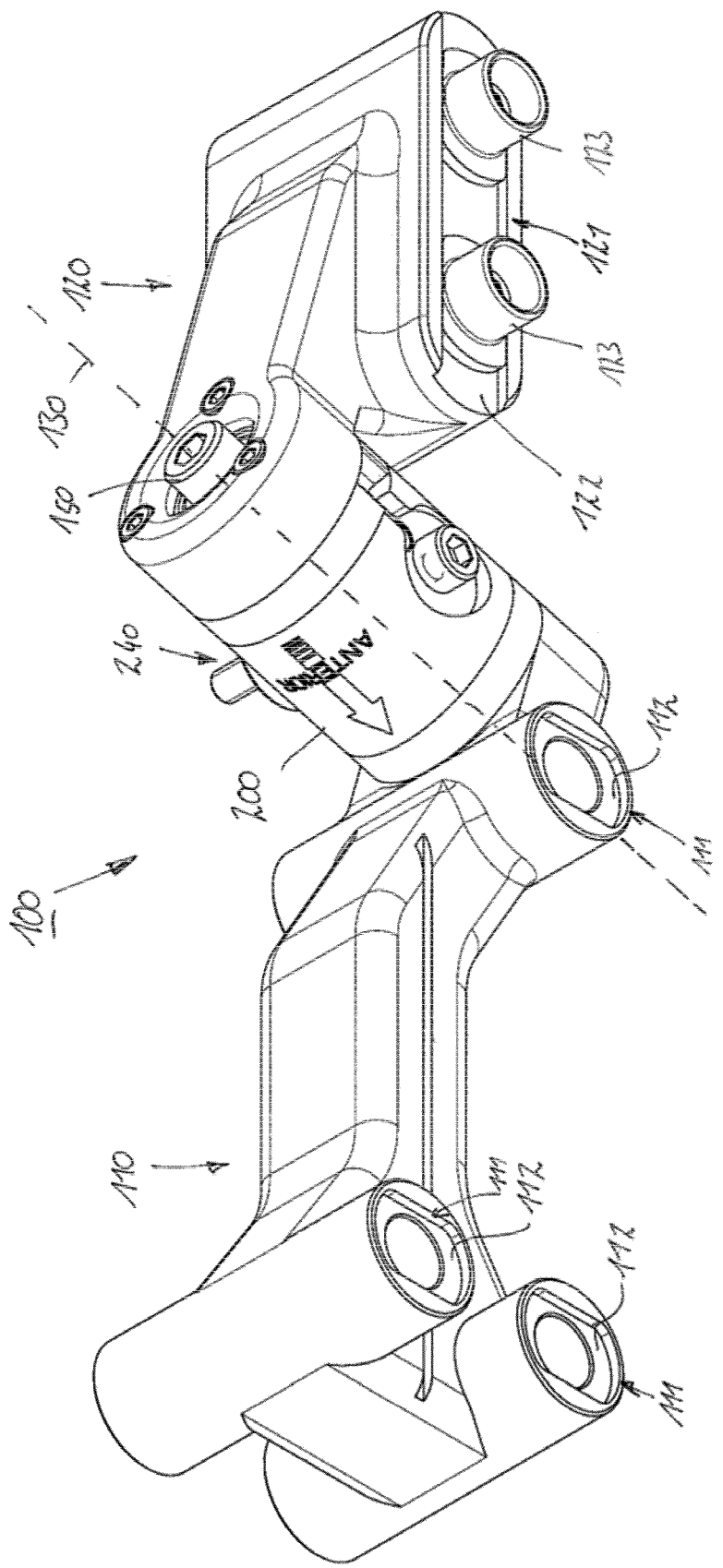
FIG. 9 shows a positioning device for the fastening elements.

FIG. 9 shows a perspective view of a positioning device 100 for positioning and aligning fastening elements 10 (not shown), which are of the kind explained for example with reference to FIG. 1. The positioning device 100 has a central body 200 on which two holders 110, 120 are arranged pivotably about a pivot axis 130. In the illustrative embodiment shown, a first holder 110 is provided for assigning and arranging the fastening elements 10 on the proximal orthosis component 21, while the second holder 120 is provided for the fastening elements 10 on the distal orthosis component 22. Both holders 110, 120 have receiving devices 111, 121, which are designed as sleeves with through-bores through which fixing elements 123 can be guided. In FIG. 9, the fixing elements 123 are shown only on the second holder 120. On the receiving devices 111, 121, bearing surfaces 112, 122 are formed for the upper face of the base 11 of the fastening elements 10. The upper face of the base 11 is the side of the base 11 lying opposite the underside 15. In the illustrative embodiment shown, all the bearing faces 112, 120 are arranged on a common holder 110, 120 in a common plane, in order to ensure that all of the fastening elements 10 lie in a common plane when they are arranged on the respective holder 110, 120 and are secured there by the fixing elements 123.

Arranged on the central body 200 is a fixing device 240 in the form of a screw via which the central body 200 is secured to the receptacle 4 which is fixed on the support 1 or the base layer 2. The longitudinal extent of the fixing device 240 runs perpendicular to the pivot axis 130 and preferably intersects the latter, such that the longitudinal axis of the fixing device 240 is orthogonal to the pivot axis 130. The longitudinal extent of the fixing device 240 is preferably flush with the longitudinal axis 3 of the joint device and of the natural joint axis or the compromise axis for the natural joint. When all of the bearing surfaces 112, 122 are located in parallel panes or in a common plane, depending on how the planes of the bearing surfaces 112, 120 are arranged, the positioning device 100 is located in a starting position. From this starting position, both the first holder 110 and the second holder 120 can be pivoted through a limited angle range, for example +/−10°, about the pivot axis 130. Joint devices 30 or also other attachment parts may be sensitive in respect of a possible angular offset of their binding sites. By means of the positioning device 100 it is possible, besides the exact positioning of the fastening elements 10 relative to each other and to a joint axis 3 about a joint device 30, to take account of this angular offset. There is the possibility of fixing the extent of the angular offset of the two holders 110, 120 in advance. For example, if a maximum offset of the planes of the binding surfaces 14 of 10° is admissible, this maximum angle range can be set with the positioning device 100. If, proceeding from the starting position, the first holder 110 is then applied to the base layer 2 and requires a pivoting in the lateral direction through 3°, proceeding from the starting position, a maximum pivot range of a further 7° in the lateral direction is available for the second holder 120. If, with such a maximum setting, a satisfactory orientation of the undersides 15 of the bases 11 of all the fastening elements 10 is not possible, the whole positioning device 100 has to be offset further laterally, or the fastening elements 10 have to be secured to the base layer via a compensating compound or a filler compound.

Figure 10:
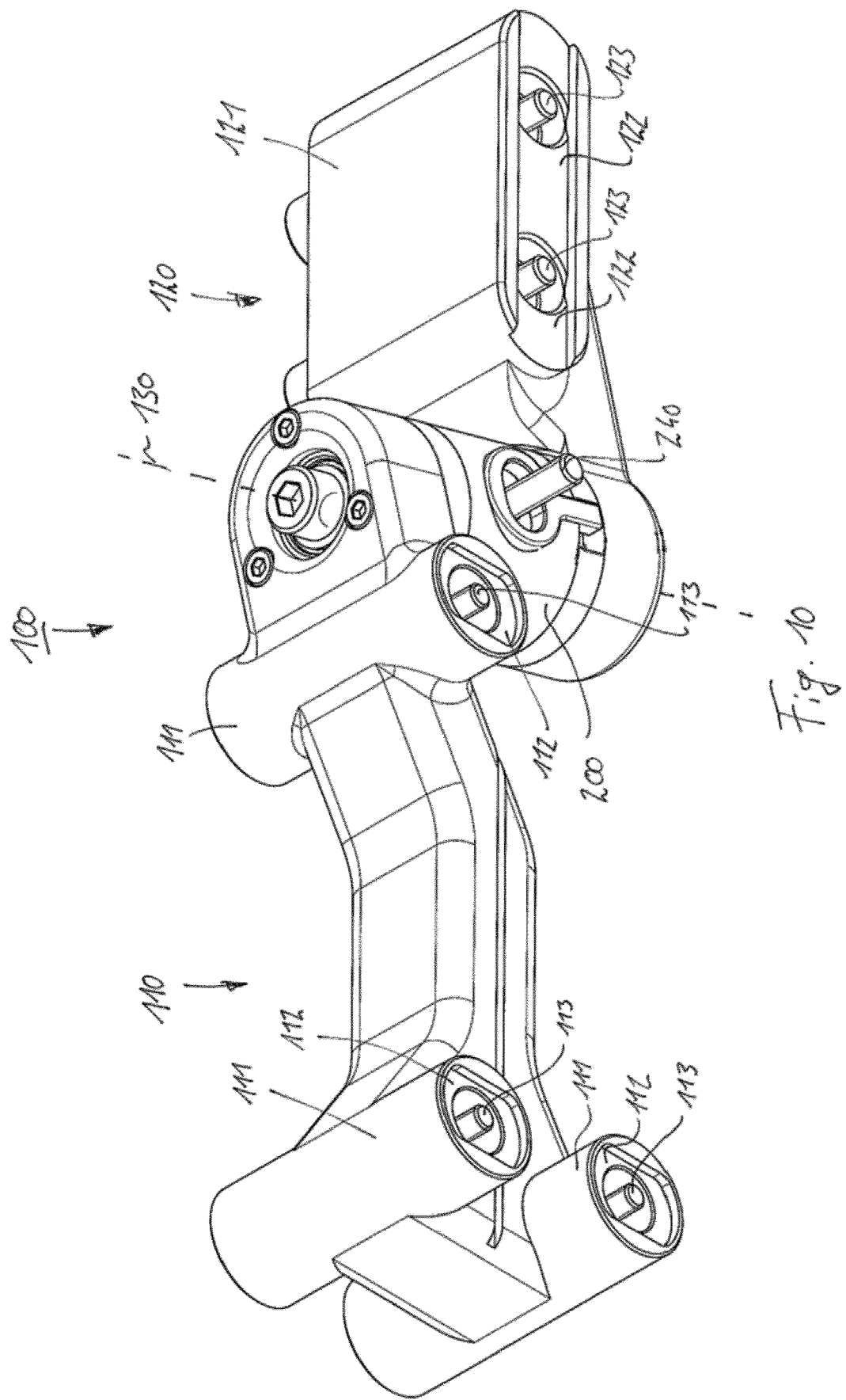
FIG. 10 shows the positioning device according to FIG. 9 in a bottom view.

The positioning device 100 is designed with axial symmetry. FIG. 9 shows an upper face, for example, while FIG. 10 shows the underside. A comparison of FIGS. 9 and 10 shows that identical receptacles for the fastening elements 10 are formed on both sides of the receiving devices 111, 112. The fixing device 240 can be removed from the central body 200 and re-inserted the other way round, such that the positioning device 100 is suitable both for a right leg and for a left leg and also for medial and also lateral positioning on base layers 2.

In FIG. 10, the fixing elements 113 in the form of screws are shown in all of the receiving devices 111. The inner threads 12 according to FIG. 1 are designed corresponding to outer threads on the fixing elements 113, so that assembly proceeds in such a way that, in each receiving device 11, the shaft 13 is inserted with the binding surfaces in front into the bores of the sleeve-like receiving devices 111. The fastening elements are fixed via the fixing elements 113. It will be seen that the shape of the bearing surfaces 112 of the receiving device 111 corresponds to the shape and contour of the bases 11, such that each fastening element is assigned and oriented in a defined manner on the respective holder 110, 120. A groove-like guide for the two bases 11 of the two fastening elements 10 is provided in the second holder 120. Further insert elements such as rails or strengthening elements or spacers can be received therein, which elements can likewise be laminated in place. After the fastening elements 10 have been fixed inside the receiving devices 111, 121, the positioning device 100 is secured with the fixing device 240 in the receptacle 4. A central screw 150 along the pivot axis 130 keeps the two holders 110, 120 in a defined position relative to each other, preferably in the starting position in which all of the undersides 15 of the fastening elements 10 are oriented relative to each other in a common plane or at least in parallel planes. When the fixing by the central screw 150 is released, the two holders 110, 120 are able to pivot about the pivot axis 130 within the predefined angle range.

Figure 11:
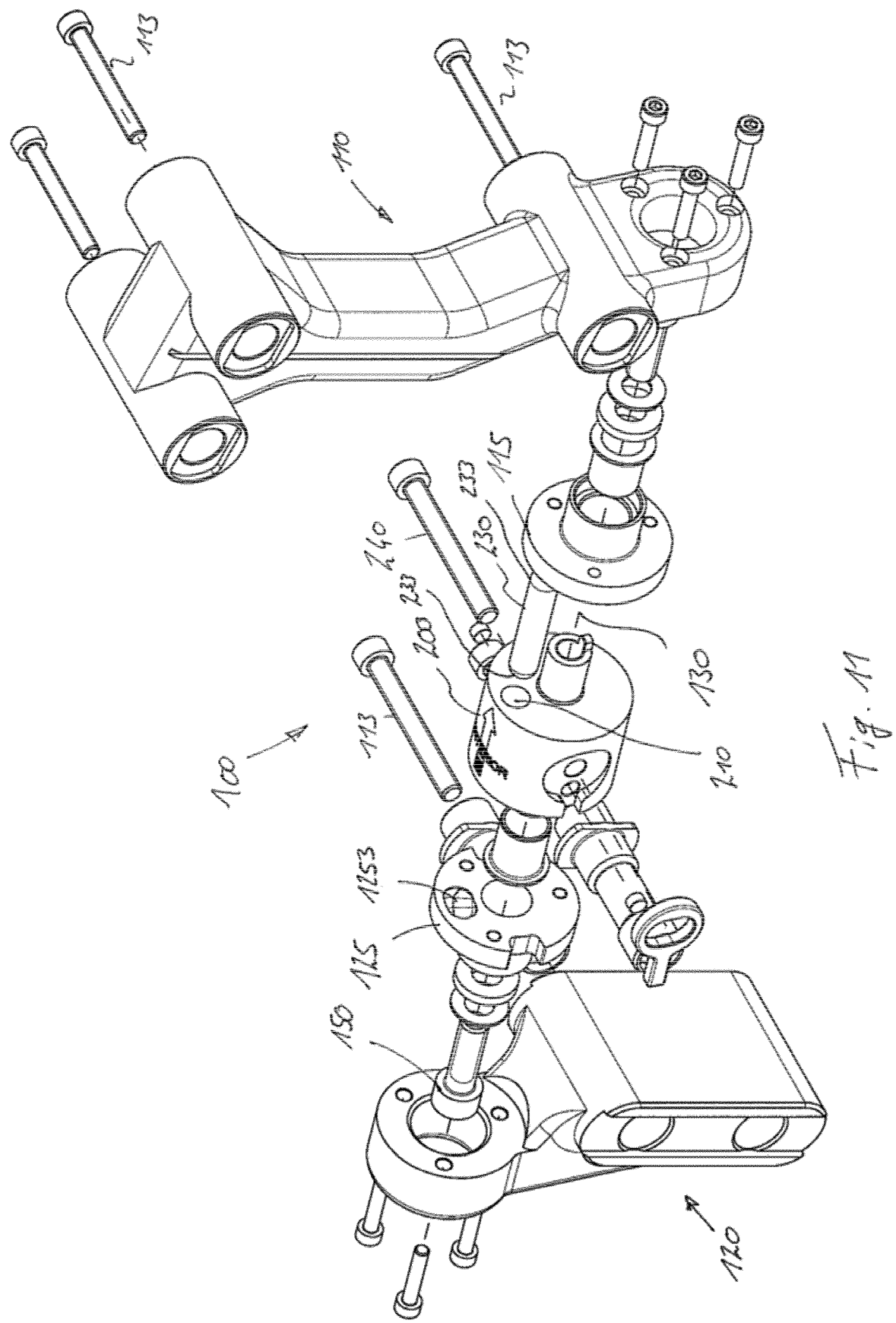
FIG. 11 shows an exploded view of the positioning device.

FIG. 11 shows an exploded view of the positioning device 100 with the central body 200, and the fixing device 240 which is guided through a bore inside the central body 200 and orthogonally intersects the pivot axis 130. The fixing elements 113 can be seen, likewise the two holders 110, 120 and the central screw 150, which extends along the pivot axis 130. Inside the central body 200, an abutment element 230 is likewise mounted longitudinally displaceably in a bore 210 in the central body 200. The bore 210 extends parallel to the pivot axis 130.

Mating pieces 115, 120 with bearing surfaces 1153, 1253, which interact with the bearing surfaces 233 at the two ends of the abutment element 230, are arranged on the holders 110, 120 via three screws. The interaction is explained below. In the illustrative embodiment shown, the mating pieces 115, 125 are mounted in a fixed position on the respective holder 110, 120. There is also the possibility, for example by means of oblong holes, to permit a rotatability of the mating pieces 115, 125 on the respective holder 110, 120. The angle range can be set via the rotation of the mating pieces 115, 125; the maximum angle range can be increased, for example, by exchanging the mating pieces 115, 125. It is likewise possible, for example by means of adjustment screws, to modify the position of the abutment surfaces 1153, 1253 in order to set the angle range about which the first holder 110 can be pivoted relative to the second holder 120 about the pivot axis 130. For this purpose, adjustment screws can be screwed into or out of the recesses in the mating piece 115, 125.

Figure 12:
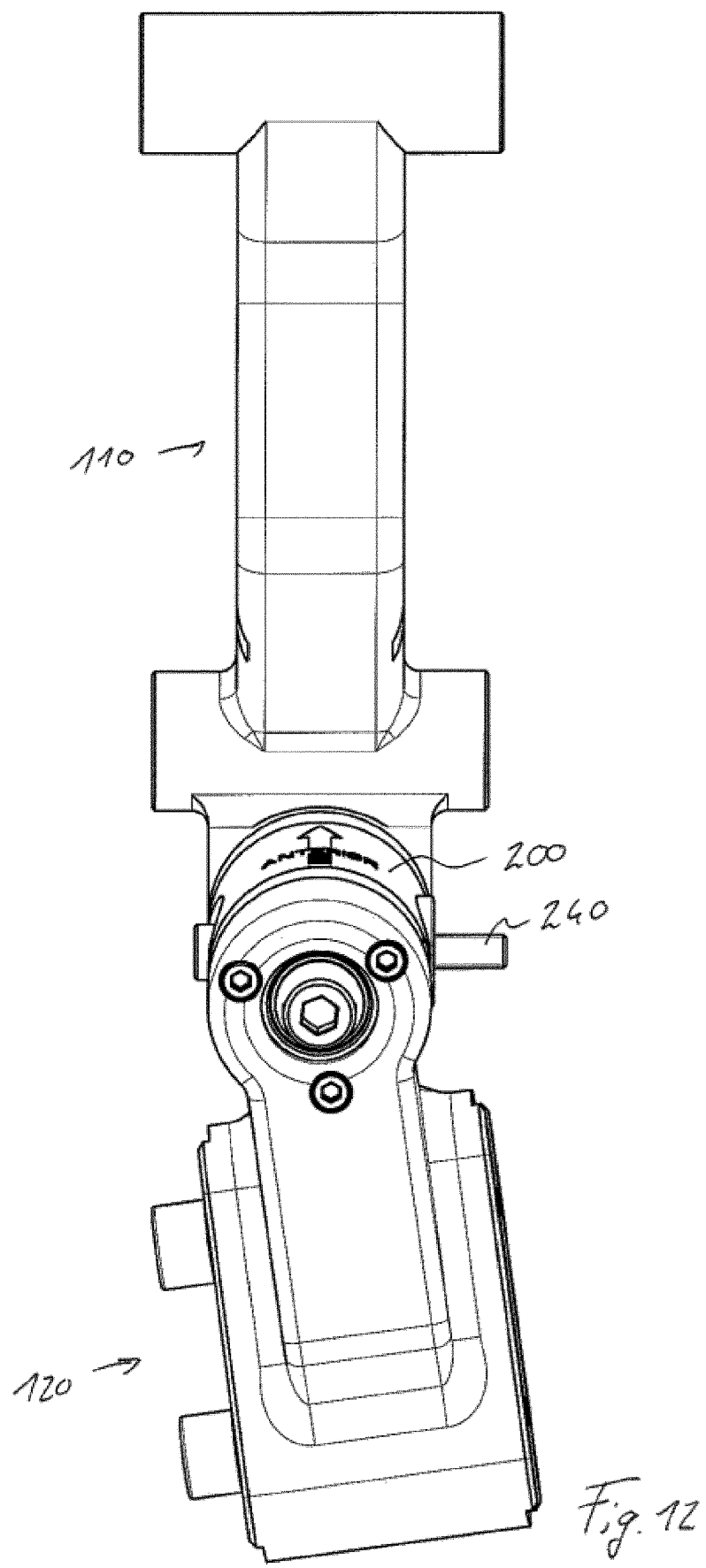
FIGS. 12 and 13 show views of holders at different angle positions.
Figure 13:
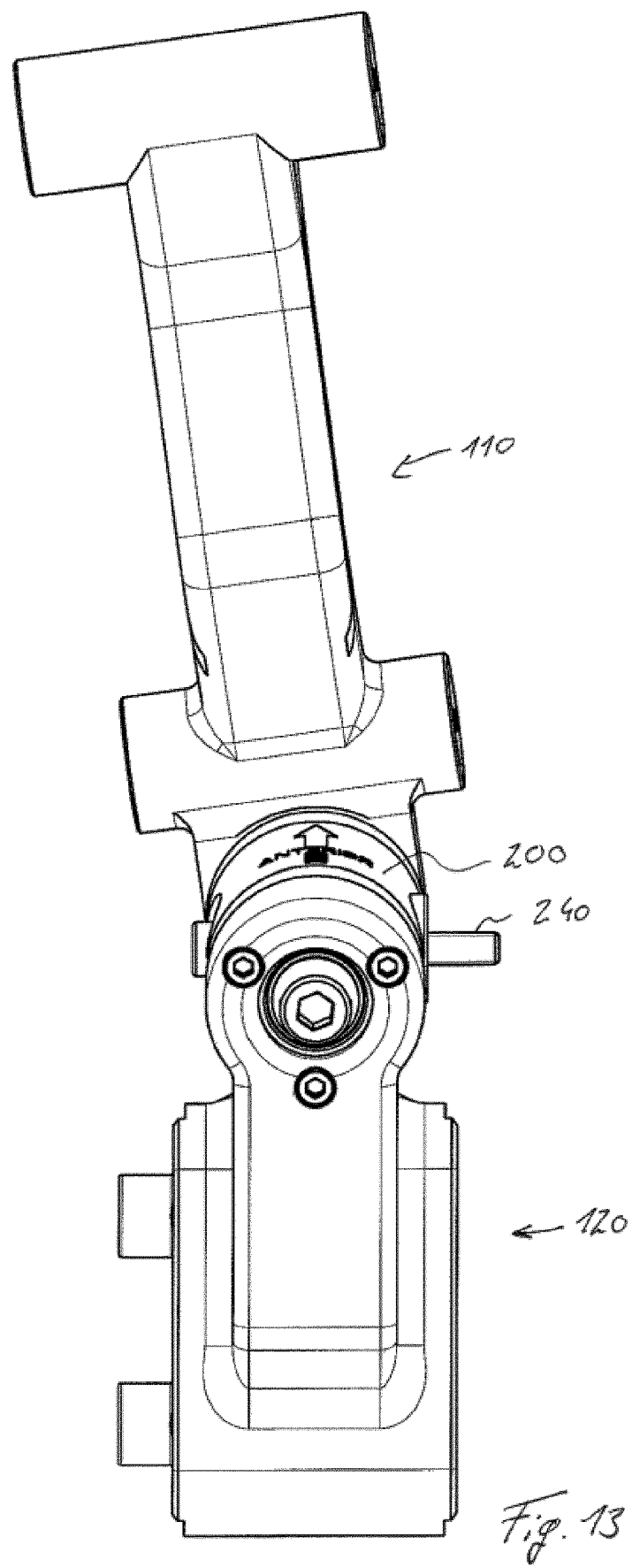

FIGS. 12 and 13 show the positioning device 100 in the same view. In FIG. 12, proceeding from the starting position, the second holder 120 is pivoted counterclockwise about the pivot axis 130 to a maximum extent. In FIG. 13, proceeding from the starting position, the first holder 110 is pivoted counterclockwise to a maximum extent. The maximum pivoting range is reached in both positions in FIGS. 12 and 13 Sectional views corresponding to FIGS. 12 and 13 are shown in FIGS. 14 and 15.

Figure 14:
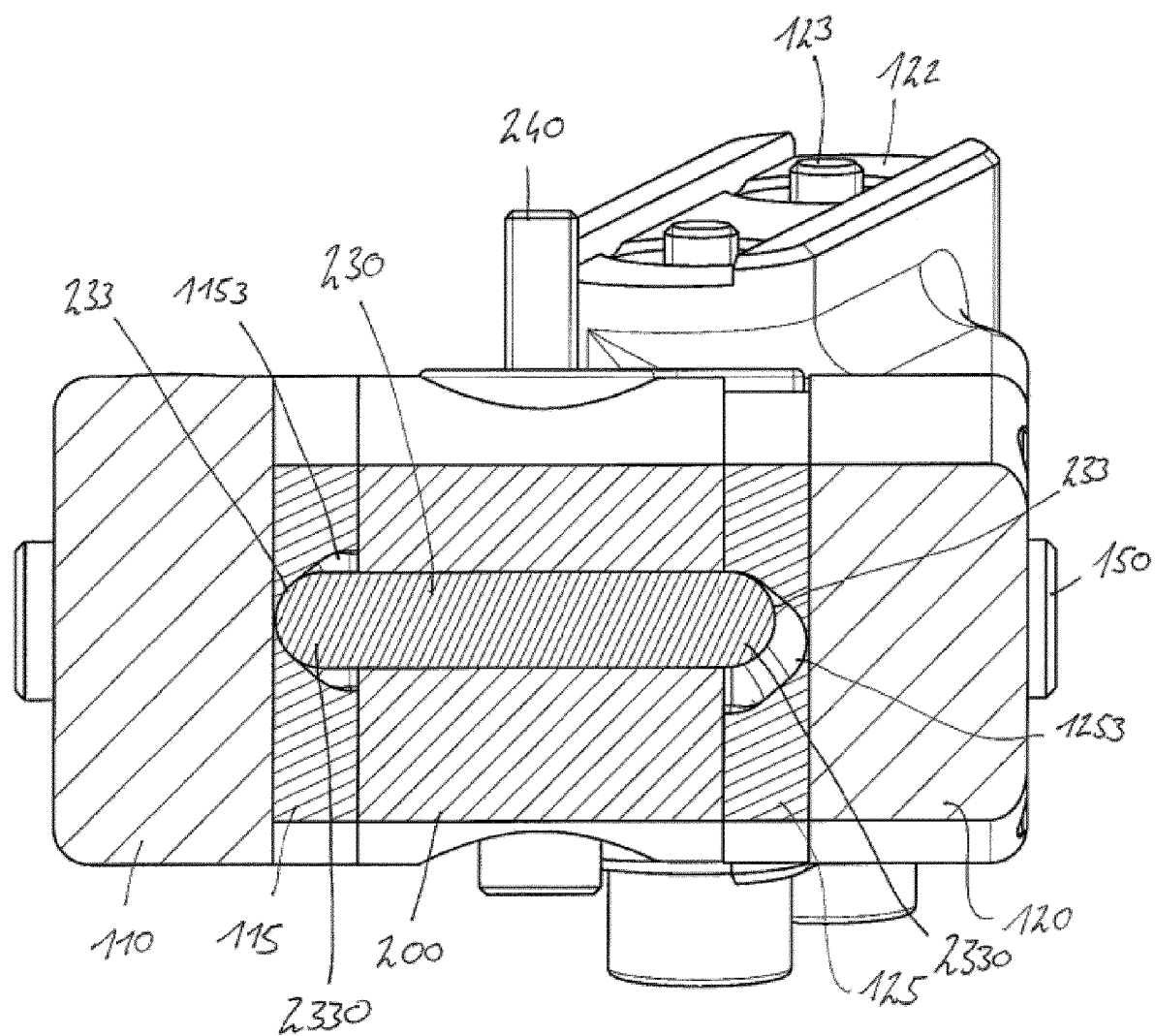
FIGS. 14 and 15 show sectional views of FIGS. 12 and 13.

FIG. 14 shows a section through the central piece 200 in the region of the abutment element 230. In the sectional view, the abutment element 230 looks like a feather key, which is arranged displaceably inside the central piece 200. In FIG. 14, a rounded end region 2330 with corresponding bearing surfaces 233 is in abutment with a correspondingly shaped bearing surface 1153 in a recess in the mating piece 115. The mating piece 115 is connected rigidly to the first holder in terms of rotation. The mating piece 115 is located in the starting position, in which the first holder 110 is correspondingly oriented. In this starting position, the abutment element 230 can be displaced to the maximum extent to the left parallel to the pivot axis 130. In this way, the right-hand end of the abutment element 230 is brought out of the free space inside the mating piece 125 of the second holder 120, such that the second holder 120 can move to the maximum extent in both directions. In the illustrative embodiment shown, the holder 120 was pivoted upward about the pivot axis, such that the bearing surface 1253 bears on the rounded bearing surface 233 of the right-hand end of the abutment element 230. If both holders 110, 120 were located in the starting position and the abutment piece 230 were located in the middle, both holders 110, 120 would be able to pivot about the pivot axis 130 by the same angle until the bearing surfaces 233, 1153, 1253 came to bear on each other. The further the abutment element 230 is displaced in one direction or the other, the more the possible angle range of the other holder increases or decreases in the one pivoting direction or the other. If the bearing surfaces 1153, 1253 of the mating pieces 115, 125 are not of the same shape or symmetrical, different angle adjustment possibilities arise. In addition to a rounded shape of the bearing surfaces 233, 1153, 1253, the latter can also have other shapes.

Figure 15:
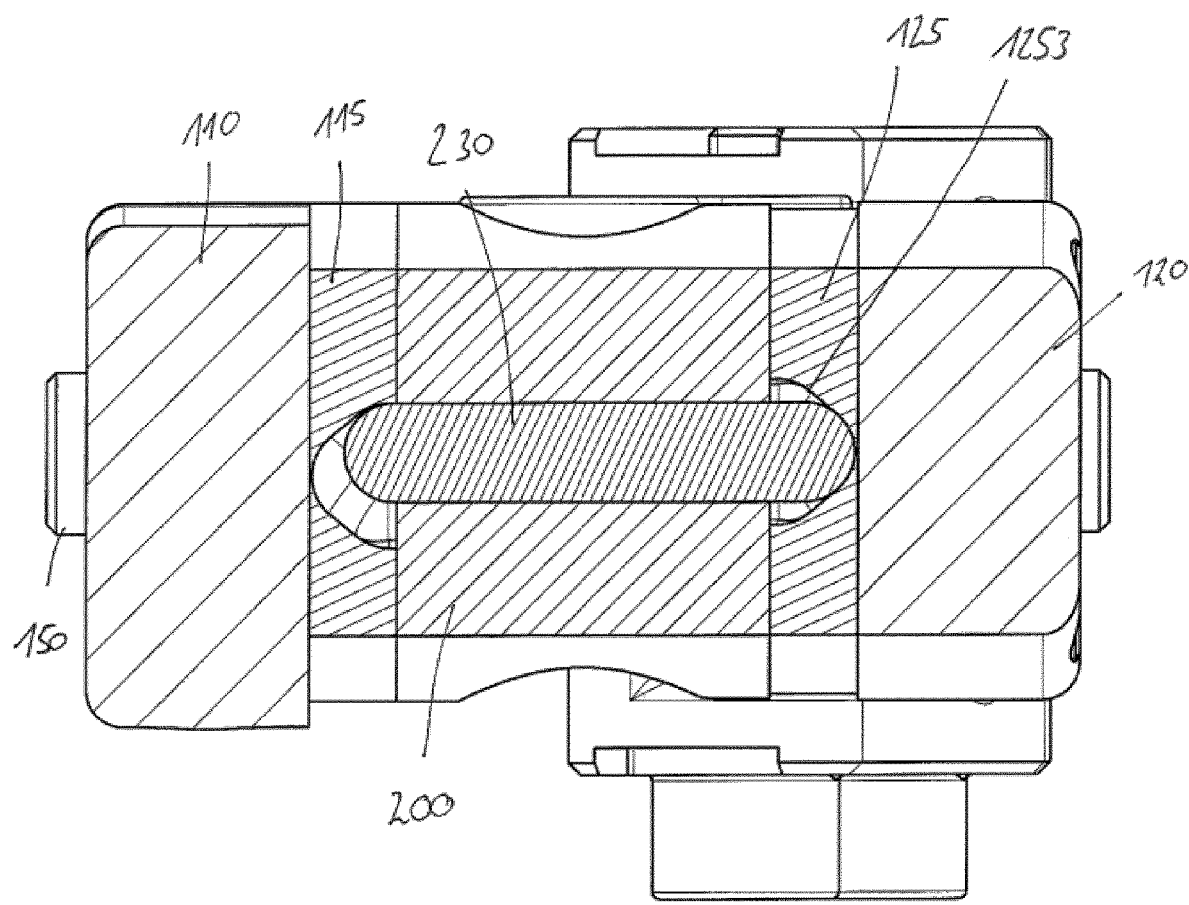

FIG. 15 shows the reverse position according to FIG. 13: the abutment element 230 has been displaced to the maximum extent to the right, as a result of which the right-hand end of the abutment element 230 lies in the recess in the mating piece 125 and thus abuts the bearing surfaces 1253. This results in a maximum pivotability of the first holder 115 about the pivot axis 130.

Figure 16:
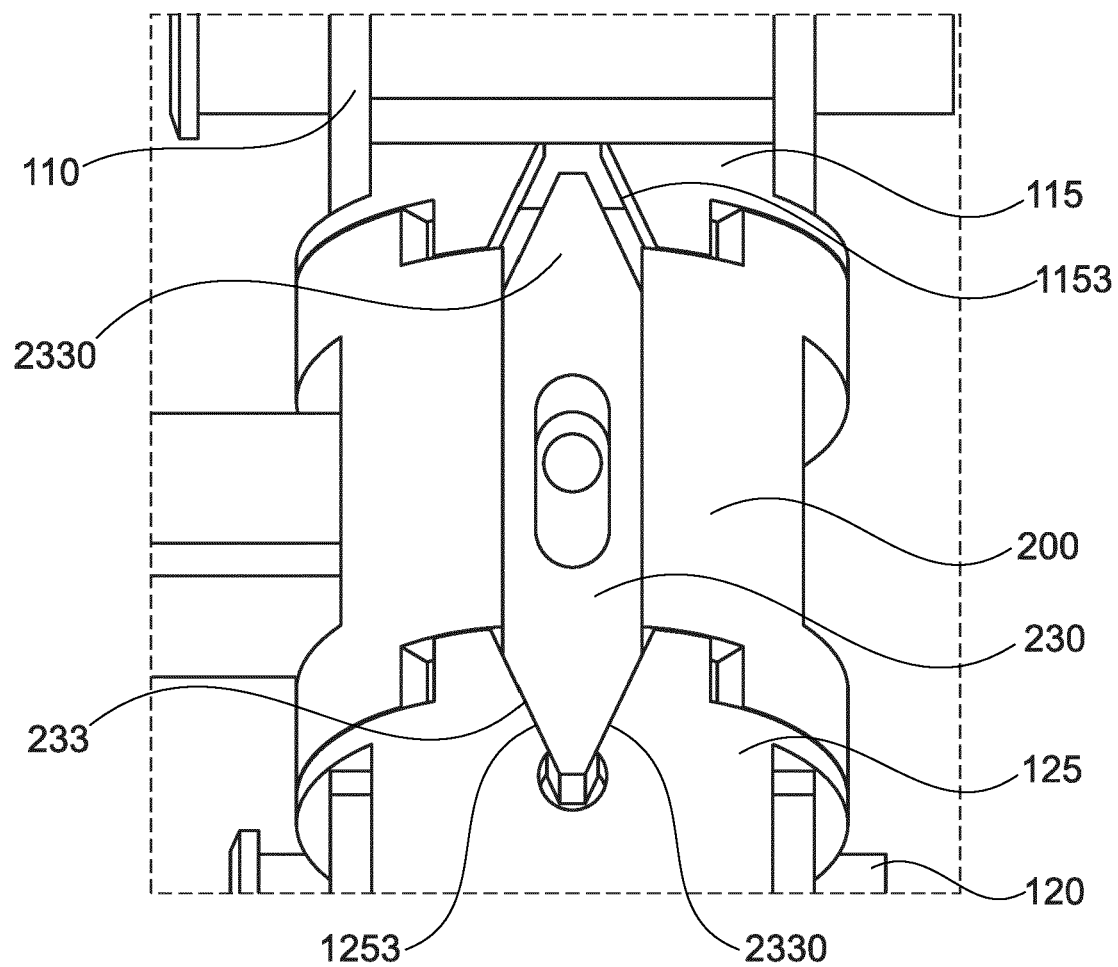
FIG. 16 shows a variant of the central piece.

An alternative embodiment of the abutment element 230 is shown in FIG. 16 in which, instead of a rounded configuration of the two end pieces 2330, a straight, conical configuration of the end pieces 2330 and of the bearing surfaces 233 is present. A corresponding conical configuration of the bearing surfaces 1153, 1253 permits a large bearing surface and therefore low surface pressure. The longitudinal displaceability of the abutment element 230 permits a simple adjustment. In the abutment element 230, an oblong hole can be present through which a screw or a movement limiter can be inserted in order to limit the adjustment range of the holders 110, 120 relative to each other. The abutment element 230 can be fixed in the respectively desired position. The oblique configuration of the bearing surfaces 233, 1153, 1253 imposes a displacement of the abutment element 230 upon contact along the displacement direction toward the opposite holder, as a result of which the adjustment angle thereof in both pivoting directions changes. The respective pivoting range of the holders can be modified within a predefined angle range according to the positions of the holders relative to each other. Provision is made that the holders 110, 120 are held securely in the respectively found optimal position in which the fastening elements 10 are placed onto the base layer 2. This can be done, for example, by clamping by the central screw 115.

We claim:

1. An orthosis or prosthesis component for receiving or for fastening to a body part, wherein the orthosis or prosthesis component comprises:
  a base layer which can be arranged on a support shaped in a manner corresponding to a shape of the body part;
  at least one fastening element having a base and a form-fit element protruding from the base, the at least one fastening element arranged on the base layer;
  wherein the base bears on or faces toward the base layer, the at least one fastening element is embedded in at least one layer of fiber composite material, and the form-fit element remains accessible from the side facing away from the base layer after the at least one fiber composite material layer has been cured, and wherein the at least one fastening element has a shaft or a form-fit element embedded in the at least one layer of fiber composite material and at least one non-embedded binding surface, wherein the shaft is configured to be oriented parallel to another shaft of another fastening element.

2. The orthosis or prosthesis component as claimed in claim 1, wherein the at least one non-embedded binding surface is configured to be oriented parallel to another of the at least one non-embedded binding surfaces.

3. The orthosis or prosthesis component as claimed in claim 1, wherein the at least one non-embedded binding surface is arranged in a plane or offset between two mutually parallel planes or arranged at an angle to another of the at least one non-embedded binding surfaces.

4. The orthosis or prosthesis component as claimed in claim 1, wherein the base layer is formed from a fiber composite material and forms a closed surface on a side facing toward the body part.

5. The orthosis or prosthesis component as claimed in claim 1, wherein the at least one fastening element is embedded non-releasably and in a manner secured against rotation.

6. The orthosis or prosthesis component as claimed in claim 1, wherein the at least one fastening element has at least one of a non-round base, projections, and recesses for securing against rotation.

7. The orthosis or prosthesis component as claimed in claim 1, wherein a thread is arranged or formed on or in the form-fit element.

8. The orthosis or prosthesis component as claimed in claim 1, wherein fastening devices are arranged thereon for securing to a body part.

9. An orthosis composed of a plurality of orthosis components as claimed in claim 1, and of at least one joint device secured to the at least one fastening element.

10. An orthosis composed of a plurality of orthosis components as claimed in claim 1, which are connected to each other to span a natural joint and have at least one predetermined separation point or a predetermined separation region in which a joint axis of the natural joint lies.

\* \* \* \* \*